United States Patent
Lee et al.

(10) Patent No.: US 11,953,444 B2
(45) Date of Patent: Apr. 9, 2024

(54) ZERO-POWER DETECTING SENSOR OF CHEMICAL SUBSTANCE AND SENSING METHOD

(71) Applicant: Korea University Research and Business Foundation, Seoul (KR)

(72) Inventors: Chulho Lee, Seoul (KR); Haeli Park, Seoul (KR)

(73) Assignee: Korea University Research and Business Foundation, Seoul (KR)

(*) Notice: Subject to any disclaimer, the term of this patent is extended or adjusted under 35 U.S.C. 154(b) by 1082 days.

(21) Appl. No.: 16/298,012

(22) Filed: Mar. 11, 2019

(65) Prior Publication Data

US 2019/0242827 A1 Aug. 8, 2019

(30) Foreign Application Priority Data

Feb. 5, 2018 (KR) .................... 10-2018-0014042

(51) Int. Cl.
| | |
|---|---|
| G01R 19/00 | (2006.01) |
| G01N 21/77 | (2006.01) |
| G01N 31/10 | (2006.01) |
| G01N 33/00 | (2006.01) |
| H01L 31/0336 | (2006.01) |
| H01L 31/109 | (2006.01) |

(52) U.S. Cl.
CPC ............ *G01N 21/77* (2013.01); *G01N 31/10* (2013.01); *H01L 31/0336* (2013.01); *H01L 31/109* (2013.01); *G01N 2021/7753* (2013.01); *G01N 33/0037* (2013.01); *G01N 33/005* (2013.01); *G01N 33/0054* (2013.01)

(58) Field of Classification Search
CPC .... G01N 21/77; G01N 31/10; G01N 33/0037; G01N 33/005; G01N 33/0054; H01L 31/022408; H01L 31/028; H01L 31/0336; H01L 31/108; H01L 31/109
USPC ......................................................... 436/164
See application file for complete search history.

(56) References Cited

U.S. PATENT DOCUMENTS

| | | | |
|---|---|---|---|
| 9,190,446 B1* | 11/2015 | Chen ................ | H01L 31/028 |
| 2005/0072673 A1* | 4/2005 | Fukuda ............. | G01N 33/005 |
| | | | 204/424 |
| 2010/0132773 A1* | 6/2010 | Lagally ............. | H01L 31/07 |
| | | | 136/255 |
| 2011/0042650 A1* | 2/2011 | Avouris ............ | H01L 31/035209 |
| | | | 257/29 |

(Continued)

FOREIGN PATENT DOCUMENTS

| | | |
|---|---|---|
| JP | 2004-85375 A | 3/2004 |
| JP | 3976700 B2 | 9/2007 |

(Continued)

OTHER PUBLICATIONS

Fan, G. et al, ACS Applied Materials & Interfaces 2011, 3, 721-725.*

(Continued)

*Primary Examiner* — Arlen Soderquist
(74) *Attorney, Agent, or Firm* — NSIP Law

(57) ABSTRACT

Disclosed are a zero-power detecting sensor of a chemical substance and a sensing method. As light is irradiated to the detecting sensor including a graphene, a light absorbing layer, and an electrode stacked, the chemical substance is detected without power.

5 Claims, 9 Drawing Sheets

(56) References Cited

U.S. PATENT DOCUMENTS

| | | | | |
|---|---|---|---|---|
| 2013/0001514 | A1* | 1/2013 | Colli | B82Y 30/00 |
| | | | | 257/21 |
| 2013/0082241 | A1* | 4/2013 | Kub | H01L 31/0336 |
| | | | | 257/21 |
| 2013/0162333 | A1* | 6/2013 | Colli | H01L 45/00 |
| | | | | 327/535 |
| 2015/0364545 | A1* | 12/2015 | Heo | H01L 29/267 |
| | | | | 257/24 |
| 2017/0256667 | A1* | 9/2017 | Lee | H01L 31/1136 |
| 2017/0345950 | A1* | 11/2017 | Sato | B82Y 10/00 |
| 2018/0138231 | A1* | 5/2018 | Kim | H01L 27/1462 |
| 2018/0197956 | A1* | 7/2018 | Lee | H01L 27/1443 |

FOREIGN PATENT DOCUMENTS

| | | |
|---|---|---|
| JP | 4742378 B2 | 8/2011 |
| JP | 5043118 B2 | 10/2012 |
| KR | 10-1507538 B1 | 4/2015 |
| KR | 10-1604792 B1 | 3/2016 |
| KR | 10-2016-0130927 A | 11/2016 |
| KR | 10-1701928 B1 | 2/2017 |
| KR | 10-1732879 B1 | 5/2017 |
| WO | WO 2006/070554 A1 | 7/2006 |

OTHER PUBLICATIONS

Jin, W. et al, Journal of Materials Chemistry 2012, 22, 2863-2867.*
Kim, H.-Y. et al, Nano Letters 2013, 13, 2182-2188.*
Gao, Z. et al, Nanoscale 2013, 5, 5576-5581.*
Zhu, M. et al, Nanoscale, 2013 2014, 6, 4909-4914.*
Pak, Y. et al, ACS Applied Materials & Interfaces 2014, 6, 13293-13298.*
Zhu, M. et al, Carbon 2015, 84, 138-145.*
Jiang, D. et al, Carbon 2016, 102, 10-17.*
Tajabadi, M. T. et al, Applied Surface Science 2016, 386, 418-426.*
Wu, Y. et al, Applied Physics Letters 2016, 109, paper 183101, 5 pages.*
Di Bartolomeo, A. et al, 2D Materials 2017, 4, paper 025075, 11 pages with 6 pages of supplementary data.*
Liu, X. et al, Advanced Functional Materials 2017, 27, paper 1702168, 30 pages.*
Singh, E. et al, ACS Applied Materials & Interfaces 2017, 9, 34544-34586.*
Periyanagounder, D. et al, Journal of Materials Chemistry C 2018, 6, 9545-9551.*
Tongay, S. et al, Applied Physics Letters 2009, 95, paper 222103, 3 pages.*
Green, M. A. et al., Progress in Photovoltiacs: Research and Applications 2010, 18, 144-150.*
Tongay, S. et al., Applied Physics Letters 2011, 99, paper 102102, 3 pages.*
Yu, J. et al, 2011 IEEE Sensors 2011, 1017-1020.*
Yatskiv, R. Carbon, 2012, 50, 3928-3933.*
Hu, P. et al, ACS Nano 2012, 6, 5988-5994.*
Georgiou, T. et al, Nature Nanotechnology 2013, 8, 100-103.*
Britnell, L. et al, Science 2013, 340, 1311-1315.*
Bernardi,, M. et al, Nano Letters 2013, 13, 3664-3670.*
Yu, W. J. et al, Nature Nanotechnology 2013, 8, 952-958.*
Yin, L. et al, Nanoscale 2014, 6, 10879-10886.*
Lee, Y. et al, Advanced Material 2015, 27, 41-46.*
Li, X. et al, Carbon 2015, 92, 126-132.*
Luo, L.-B. et al, Journal of Materials Chemistry C 2015, 3, 4723-4728.*
Chen, C. et a, Scientific Reports 2015, 5, paper 11830, 9 pages.*
Sata, Y. et al, Applied Physics Letters 2015, 107, paper 023109, 5 pages.*
Lu, R. et al, Scientific Reports 2016, ∧. paper 19161, 7 pages.*
De Fazio, D. et al, ACS Nano 2016, 10, 8252-8262.*
Xie, C. et al, Advanced Functional Materials 2017, 27, paper 1603886, 41 pages.*
Yu, W. et al, Small 2017, 13, paper 1700268, 8 pages.*
Tao, L. et al, 2D Materials and Applications 2017, 1, paper19, 8 pages.*
Perumal, P. et al, Scientific Reports 2017, 7, paper 10002, 9 pages.*
Liu, Y. et al, ACS Applied Materials & Interfaces 2017, 9, 36137-36145.*
Tian, W. et al, Small 2017, 13, paper 1701848, 22 pages.*
Sahatiya, P. et al, Nanotechnology 2017, 28, paper 455204, 11 pages.*
Li, J. et al, ACS Applied Materials & Interfaces 2017, 9, 42779-42787.*
Esfandiar, A. et al, International Journal of Hydrogen Energy 2012, 37, 15423-15432.*
Late, D. J. et al, ASC Nano 2013, 7, 4879-4891 and 37 pages of supporting information.*
Yang, S. et al, Nanoscale 2014, 6, 2582-2587 and 4 pages of supplementary material.*
Zhang, W. et al, Scientific Reports 2014, 4, paper 3826, 8 pages.*
Uddin, M. A. et al, Nanotechnology 2014, 25, psper 125501, 9 pagesand one page of supplementary data.*
Huo, N. et al, Scientific Reports 2014, 4, paper 5209, 9 pages.*
Kim, J. et al, Scientific Reports 2014, 4, paper 5384, 5 pages with 5 pages of supplementary information.*
Moriya, R. et al, Applied Physics Letters 2014, 105, paper 083119, 4 pages.*
Hoffmann, M. W. G. et al, Advanced Materials 2014, 26, 8017-8022 with 13 pages of supporting information.*
Cho, B. et al, ACS Applied Materials & Interfaces 2015, 7, 16775-16780 with 10 pages of supporting information.*
Niu, Y. et al, Carbon 2015, 95, 34-41 with 4 pages of supporting information.*
Huo, N. et al, Small 2015, 11, 5430-5438 with 11 pages of supporting information.*
Cho, B. et al, Sensors 2015, 15, 24903-24913 with 2 pages of supplementary information.*
Zhang, J. et al, Advanced Materials 2016, 28, 795-831.*
Kim, W. et al, Advanced Materials 2016, 28, 1845-1852 with 8 pages of supporting information.*
Yue, N. et al, Journal of Materials Chemistry A 2016, 4, 8198-8203 with 3 pages of supporting information.*
Jia, Y. et al, Nanoscale Research Letters 2016, 11, paper 299, 6 pages.*
Yue, N. et al, Journal of Materials Chemistry C 2017, 5, 5887-5896 with 13 pages of supplementary information.*
Bai, Z. et al, Journal of Alloys and Compounds 2017, 726, 803-809.*
Liu, L. et al, Nanoscale 2017, 9, 18579-18583 with 3 pages of supplementary information.*
Comini, E. et al, Proceedings 2017, 1, paper 469, 4 pages.*
Choi, H. K. et al, Nanoscale 2017, 9, 18644-18650 with 11 pages of supplementary information.*
Mu, C. et al, Journal of Materials Research 2017, 32, 4115-4131.*
Su, P.-G. et al, Sensors and Actuators B 2018, 254, 1125-1132.*
Chen, M. et al, Carbon, 2018, 130, 281-287.*
Yi, J. et al, Sensors and Actuators B 2011, 155, 264-269.*
Tongay, S. et al, Physical Review X 2012, 2, paper 011002, 10 pages.*
Hoffmann, M. W. G. et al, Nano Energy 2013, 2, 514-522.*
An, X. et al, Nano Letters 2013, 13, 909-916 with 6 pages of supplementary information.*
Britnell, L. et al, Science 2013, 340, 1311-1314 with 12 pages of supplementary materials.*
Singh, A. et al, Small 2014, 10, 1555-1565 with 5 pages of supporting information.*
Cao, Y. et al, Small 2014, 10, 2345-2351 and 10 pages of supporting information.*
Lee, C.-H. et al, Nature Nanotechnology 9, 676-681 and 16 pages of supplementary information.*
Nallon E. C. et al, Sensors and Actuators B 2014, 190, 578-584.*
Hsueh, H.-T. et al, IEEE Electron Device Letters 2014, 35, 1272-1274.*

(56) References Cited

OTHER PUBLICATIONS

Litvinenko, S. V. et al, Sensors and Actuators A 2015, 224, 30-35.*
Luo, W. et al, Advance Optical Materials 2015, 3, 1418-1423 and 12 pages of supporting information.*
Di Bartolomeo, A., Physics Reports 2016, 606, 1-58.*
Vashpanov, Y., AASCIT Communications 2016, 3, 90-94.*
Oz, S. et al, Solar Energy Materials & Solar Cells 2016, 158, 195-201 and 2 pages of supplementary material.*
Long, H. et al, Advanced Functional Materials 2016, 26, 5158-5165 and 4 pages of supporting information.*
Gad, A. et al, ACS Sensors 2016, 1, 1256-1264.*
Lee, J. Y. et al, Nanomaterials 2016, 6, paper 193, 18 pages.*
Wei, X. et al, Nanoscale, 2017, 9, 8388-8392 with 7 pages of supplementary information.*
Yan, F. et al, Nanotechnology 2017, 28, paper 271T01, 8 pages with 9 pages of supplementary information.*
Nallon, E. C. et al, Electronics 2017, 6, paper 55, 7 pages.*
Chen, H. et al, Small 2018, 14, paper 1702571, 7 pages with 4 pages of supporting information.*
Lv, Q. et al, Advanced Optical Materials 2018, 6, paper 1700490, 6 pages with 7 pages of supporting information.*
Zhou, X. et al, Advanced Functional Materials 2018, 28, paper 1706587, 28 pages.*
Feng, W. et al, 2D Materials 2018, 5, paper 025008, 6 pages.*
Miao, X. et al, Nano Letters 2012, 12, 2745-2750.*
Loan, P. T. K. et al, Advanced Materials 2014, 26, 4838-4844.*
Li, X. et al, Nano Energy 2015, 16, 310-319.*
Yeh, C.-H. et al, ACS Applied Materials & Interfaces 2017, 9, 36181-36188.*
Schedin, F. et al, Nature Materials 2007, 6, 652-655.*
Lu, G. et al, Nanothechnology 2009, 20, paper 445502, 9 pages.*
Chung, M. G. et al, Sensors and Actuators B 2012, 169, 387-392.*
Kim, K.-S. et al, Sensors and Actuators B 2014, 193, 42-45.*
Karaduman, I. et al, Materials Science in Semiconductor Processing 2014, 28, 43-47.*
Phan, D.-T. et al, Sensors and Actuators B 2015, 210, 661-668.*
Wan, X. et al, 2D Materials and Applications 2017, 1 paper 4, 8 pages with 5 pages of supplemental materials.*
Yuriy, Y., XXIV International Conference on Automated Control 2017, 62-64.*
Ko, G. et al, Current Applied Physics 2010, 10, 1002-1004. (Year: 2010).*
Vashpanov, Y. et al, Sensors 2011, 11, 1321-1327. (Year: 2011).*
Chen, G. et al, Applied Physics Letters 2012, 101, paper 053119, 4 pages with 6 pages of supplemental material. (Year: 2012).*
Duesberg, G. S. et al, 2013 Proceedings of the European Solid-State Device Research Conference (ESSDERC) 2013, 85-90. (Year: 2013).*
Cho, B. et al, Journal of Materials Chemistry C 2014, 2, 5280-5285 with 7 pages of supplemental information. (Year: 2014).*
Du, Y. et al, Materials Letters 2014, 135, 151-153. (Year: 2014).*
Uddin, M. A. et al, Proceedings of the 14th IEEE International Conference on Nanotechnology 2014, 554-557. (Year: 2014).*
Fattah, A. et al, IEEE Sensors Journal 2014, 14, 4104-4108. (Year: 2014).*
Rigoni, F. et al, Scientific Reports 2017, 7, paper 44413, 12 pages with 3 pages of supplementary information. (Year: 2017).*
Zhu, M. et al, Nanoscale 2014, 6, 4909-4914. (Year: 2014).*
Fattah, A. et al, Small 2014, 10, 4193-4199. (Year: 2014).*
Quang, V. V. et al, Sensor Letters 2015, 13, 381-386. (Year: 2015).*
Chen, Z. et al, Advanced Optical Materials 2015, 3, 1207-1214 with 6 pages of supporting information. (Year: 2015).*
Riazimehr, S. et al, Solid-State Electronics 2016, 115, 207-212. (Year: 2016).*
Li, X. et al, Small 2016, 12, 595-601 with 7 pages of supporting information. (Year: 2016).*
Li, G. et al, Small 2016, 12, 5019-5026 with 4 pages of supporting information. (Year: 2016).*
Wan et al., "A self-powered high-performance graphene/silicon ultraviolet photodetector with ultra-shallow junction: breaking the limit of silicon?" 2D Materials and Applications, Apr. 11, 2017, (8 pages in English).
Shim et al., "Large-Area Single-Layer MoSe$_2$ and Its van der Waals Heterostructures," ACS Nano, Jul. 2, 2014, 8 (7), pp. 6655-6662.
Neri, Giovanni., "Thin 2D: The New Dimensionality in Gas Sensing", *Chemosensors*, vol. 5, Issue 3,2017 (20 pages in English).

* cited by examiner

ZERO-POWER DETECTING SENSOR OF CHEMICAL SUBSTANCE AND SENSING METHOD

CROSS-REFERENCE TO RELATED APPLICATIONS

A claim for priority under 35 U.S.C. § 119 is made to Korean Patent Application No. 10-2018-0014042 filed on Feb. 5, 2018, in the Korean Intellectual Property Office, the entire contents of which are hereby incorporated by reference.

BACKGROUND

Embodiments of the inventive concepts described herein relate to a zero-power detecting sensor of a chemical substance and a sensing method, and more particularly, relate to a zero-power detecting sensor of a chemical substance including detecting a target material depending on a change of a photocurrent in a graphene-based vertical heterojunction structure, which has an atomic layer thickness and is capable of generating the photocurrent in response to light, and a sensing method.

In recent years, interest in harmful gas and atmospheric environment in human living environment has been heightened, and it is important to recognize need of a sensor capable of easily detecting environmentally harmful gas or other specific chemical substances.

In addition, as the age of the fourth industrial revolution characterized by super-connectivity and super-intelligence has come, a role of internet of things (IoT) through intelligence of things becomes important, and a detecting sensor plays a primary role in obtaining information for the internet of things.

Important points of the detecting sensor are not only general performance such as sensitivity, selectivity, reaction time, recovery speed, or the like, but also power consumption.

If power consumption of the sensor is minimized within a limited power capacity, use time of a product is capable of being maximized. Thus, related research must be conducted in order that the sensor is applied to the internet of things.

However, a conventional gas sensor of a resistance type has limitation in minimizing the power consumption because a driving voltage is applied to measure a resistance change.

To solve this problem, technical development of the sensor, which operates without the power consumption to be capable of detecting the chemical substance, and a sensing method has been demanded.

SUMMARY

Aspects of the present disclosure are to address at least the above-mentioned problems and/or disadvantages and to provide at least the advantages described below. Embodiments described herein provide a detecting sensor, which detects a chemical substance without a driving voltage and is capable of operating without power.

In additional, embodiments described herein provide a detecting sensor capable of detecting a chemical substance by a photocurrent change, in which a Fermi energy level is changed by the chemical substance adsorbed or desorbed on a surface of a graphene and the amount of the photocurrent in the detecting sensor is changed.

Embodiments of the inventive concepts provide a method of sensing a chemical substance without power including detecting the chemical substance without the power as light irradiated to a detecting sensor including a graphene, a light absorbing layer, and an electrode stacked.

According to an exemplary embodiment, a built-in potential is generated by a Fermi energy level difference at a Shottky junction interface of the graphene and the light absorbing layer, a photocurrent is generated as light of bandgap energy or more is irradiated to the light absorbing layer, and the photocurrent increases or decreases based on presence of the chemical substance.

According to an exemplary embodiment, the Fermi energy level is changed by adsorbing or desorbing the chemical substance on the surface of the graphene, and presence of the chemical substance is detected.

According to an exemplary embodiment, catalyst materials may be formed on the surface of the graphene to detect a specific chemical substance among chemical substances. For detecting hydrogen, Pd or Pt is deposited on the surface of the graphene, thereby detecting presence of a hydrogen material.

Embodiments of the inventive concepts provide a zero-power detecting sensor of a chemical substance including a graphene, a light absorbing layer, and an electrode stacked, wherein the graphene and the light absorbing are formed in a heterojunction structure.

According to an exemplary embodiment, the light absorbing layer includes a semiconductor or a transition metal chalcogen compound.

According to an exemplary embodiment, the semiconductor includes at least one selected from the group consisting of Si, a GaN compound, a GaAs compound, a copper indium gallium selenide (CIGS) compound, a perovskit compound, and a black phosphorous, and the transition metal chalcogen compound includes at least one selected from the group consisting of $MoS_2$, $MoSe_2$, $MoTe_2$, $WS_2$, $WSe_2$, $WTe_2$, $SnS_2$, $InSe$, $In_2Se_3$, $GaS$, $GaSe$, $HfS_2$, $HfSe_2$, $ZrS_2$, $ZrSe_2$, and $HfSe_2$.

According to an exemplary embodiment, catalyst materials may be formed on the surface of the graphene to detect a specific substance among chemical substances. For detecting hydrogen, Pd or Pt is deposited on the surface of the graphene to detect presence of a hydrogen material.

According to an exemplary embodiment, presence of the chemical substance is detected by a Fermi energy level change as the chemical substance is adsorbed or desorbed on the surface of the graphene.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
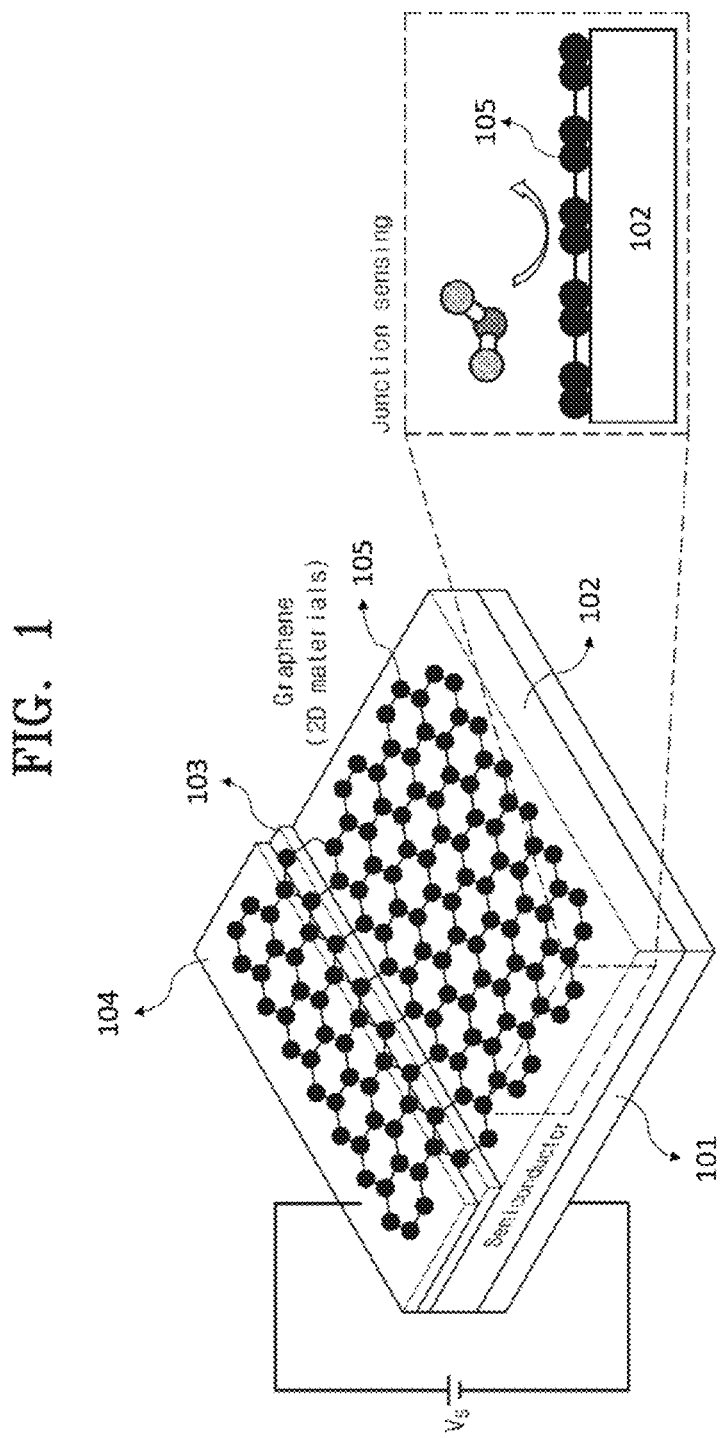
FIG. 1 is a schematic view illustrating a detecting sensor according to an embodiment of the present disclosure.

Hereinafter, embodiments of the present disclosure will be described in detail with reference to the accompanying drawings. The embodiment of the present disclosure may be modified in various forms, and the scope of the present disclosure should not be construed as being limited to the following embodiments. These embodiments are provided to more fully describe the present disclosure to those skilled in the art. Thus, shapes of elements of the drawings have been exaggerated to emphasize a clearer description.

A chemical substance described in the present disclosure refers to a gas or liquid substance, which is present in nature.

A zero-power detecting sensor of a chemical substance according to the present disclosure includes a graphene, a light absorbing layer, and an electrode stacked vertically, and is a sensor operating without power where the graphene and the light absorbing layer are heterogeneously junctioned to each other.

In the present disclosure, the light absorbing layer is bonded to a bottom of the graphene in a heterojunction structure, a photoreaction is generated without power when light is irradiated to an interface between the graphene and the light absorbing layer, and a change of the interface is sensed to detect presence of the chemical substance.

The detecting sensor of the present disclosure includes the heterojunction between the graphene and the light absorbing layer, and the graphene-light absorbing layer may include (1) a graphene-semiconductor, (2) a graphene-transition metal chalcogen compounds (TMDCs).

As the graphene of the detecting sensor of the present disclosure adsorbs or desorbs the chemical substance, a photocharge is generated or separated in the interface between the graphene and the light absorbing layer upon light irradiation, and therefore a photocurrent flows.

Since the graphene has a thin thickness, a Fermi level of the graphene is changed by the chemical substance adsorbed or desorbed on a surface of the graphene. A change of the Fermi level affects a built-in potential of the interface between the graphene and the light absorbing layer, and the amount of the photocurrent is changed.

Catalyst materials may be additionally formed on the surface of the graphene to detect a specific chemical substance among chemical substances.

For example, Pd or Pt is deposited on the surface of the graphene for detecting hydrogen.

Since hydrogen has no polarity, it is difficult to adsorb onto the surface of the graphene. To this end, Pd or Pt is thinly deposited on the surface of the graphene and allows hydrogen to be adsorbed well, thereby sensing hydrogen among the chemical substances.

Also, the light absorbing layer serves to separate electrons and holes when given light of bandgap energy or more.

The light absorbing layer may include a semiconductor or a transition metal chalcogen compound.

In the present disclosure, Si, a GaN compound, a GaAs compound, a copper indium gallium selenide (CIGS) compound, a perovskite compound, a black phosphorous, or the like may be used as the semiconductor capable of being used as the light absorbing layer, desirably.

Also, $MoS_2$, $MoSe_2$, $MoTe_2$, $WS_2$, $WSe_2$, $WTe_2$, $SnS_2$, $InSe$, $In_2Se_3$, $GaS$, $GaSe$, $HfS_2$, $HfSe_2$, $ZrS_2$, $ZrSe_2$, $HfSe_2$, or the like may be used as the transition metal chalcogen compound, desirably.

The electrode may function as a path, where the photocurrent generated by light flows, in the detecting sensor.

The electrode may include a metal or a graphene. Metals used as a usual electrode may be used as the electrode, and Au, Ag, Al, Cr, Co, Pd, Pt, Ti, Ta, Cu, Sc, Ni, Mo, Fe, or the like may be used as the electrode. Also, a metallic graphene may be used as the electrode.

The electrode is disposed below the light absorbing layer and is electrified between the graphene and the light absorbing layer. In this case, when the photocurrent is generated by light, the graphene functions as an electrode, and therefore electricity flows between the graphene and the electrode disposed below the light absorbing layer.

In addition, the electrode 101, 104 may be formed on the bottom and top of the light absorbing layer 102 in contact with the graphene 105. In this case, for insulating the electrode 104 disposed on the top of the light absorbing layer 102 in contact with the graphene 105 from the light absorbing layer 102, an insulating layer 103 may be formed between the electrode 104 disposed on the top of the light absorbing layer 102 and the light absorbing layer 102. (See FIG. 1)

In the present disclosure, the chemical substance may be detected by operating the detecting sensor without power, and the detecting sensor may detect a change of the interface between the graphene and the light absorbing layer.

When the graphene and the light absorbing layer are junctioned to each other in a powerless state, the built-in potential is generated by a difference of the Fermi energy level at a Schottky junction interface, the photocharge is generated and separated when light of bandgap energy or more is irradiated to the light absorbing layer, and therefore the photocurrent flows.

The detecting sensor operates due to the photocurrent, the graphene is changed into a p-doped or n-doped state when the chemical substance is adsorbed on the surface of the graphene, the built-in potential between the graphene and the light absorbing layer is changed, and then the amount of the photocurrent is changed.

Figure 2:
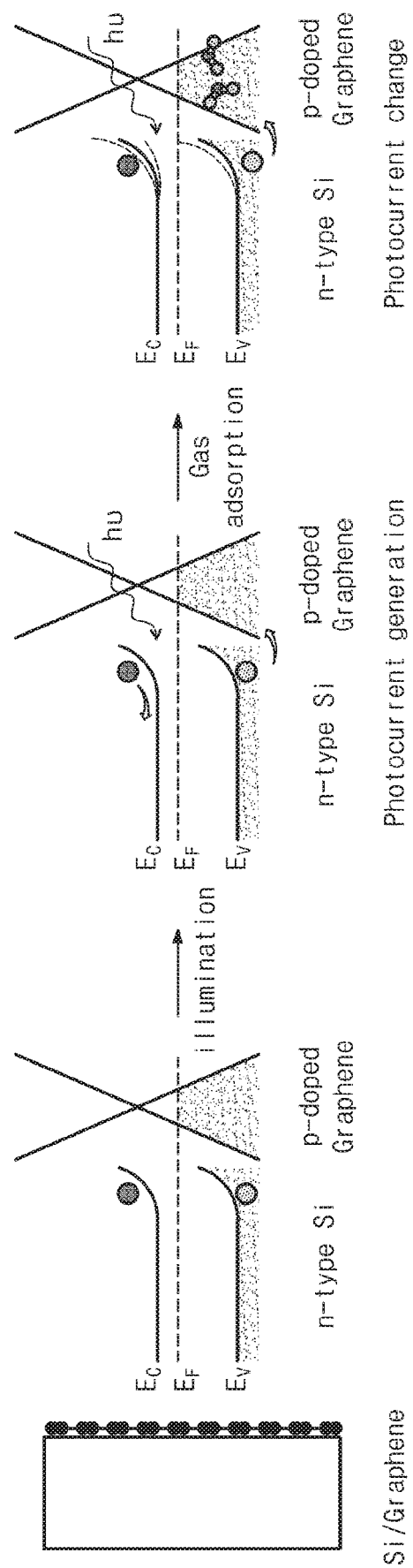
FIG. 2 is a view illustrating an operating and sensing mechanism of a detecting sensor of the present disclosure.

FIG. 2 is a view illustrating an operating and sensing mechanism of a detecting sensor according to an embodiment of the present disclosure.

The sensing mechanism is to confirm presence of the chemical substance by detecting the change between the graphene and a semiconductor n-Si functioning as a photocurrent layer.

Referring to FIG. 2, when the graphene and the n-Si (the semiconductor) are junctioned to each other, the built-in potential is generated at the interface therebetween by a work function difference. When light having bandgap energy of the n-Si or more is irradiated, the photocharge is generated/separated, and therefore the photocurrent flows.

Thus, the detecting sensor may operate at even 0V. When the chemical substance such as a gas is adsorbed on the surface of the graphene, the graphene is changed into the p-doped or n-doped state based on a type of the gas, and therefore the built-in potential between the graphene and the n-Si is changed so that the amount of the photocurrent is changed.

Namely, as the surface of the graphene is changed into the p-doped or n-doped state, the Fermi energy level is changed.

Therefore, as the amount of the photocurrent increases or decreases, presence of the chemical substance may be confirmed.

Subsequently, the adsorbed gas molecules are released, and then the work function of the graphene is returned to its original state.

Hereinafter, Examples of the present disclosure will be described.

Example 1

A metallic graphene was prepared, and an n-Si semiconductor material was prepared as a light absorbing layer, and then a heterojunction of the metallic graphene and the n-Si semiconductor material was carried out.

To carry out the heterojunction, the graphene grew on a copper foil by a CVD process. Here, the graphene thinly grew in two dimensions. Then, PMMA coating was carried out on the copper foil where the graphene grew. After the PMMA coating was completed, the copper foil was dissolved and removed using an ammonium persulfate solution.

When the copper foil was removed, the graphene was attached to a bottom of the PMMA. The PMMA where the graphene was attached was placed in the water and was disposed on an n-Si functioning as a light absorbing layer, thereby being attached to the n-Si. The PMMA was dissolved and removed using acetone.

An electrode was attached on the n-Si attached to the graphene, and an Au electrode was used as the electrode.

Dry air flowed in a closed space while light was irradiated to the detecting sensor manufactured by the above-described method. After dry air flowed for 500 seconds, NH3 of 50 ppm flowed for 500 seconds. After that, dry air flowed again for 500 seconds, and then NH3 of 50 ppm flowed for 500 seconds. The above processes were repeated until 4,000 seconds.

Example 2

Example 2 was carried out the same as Example 1, except that NO2 of 5 ppm instead of NH3 was used as a chemical substance.

Example 3

Example 3 was carried out the same as Example 1, except that Pd was deposited on the surface of the graphene after the heterojunction of the graphene and the n-Si, upon manufacturing the detecting sensor. H2 of 50 ppm was used as a chemical substance.

Figure 3A:
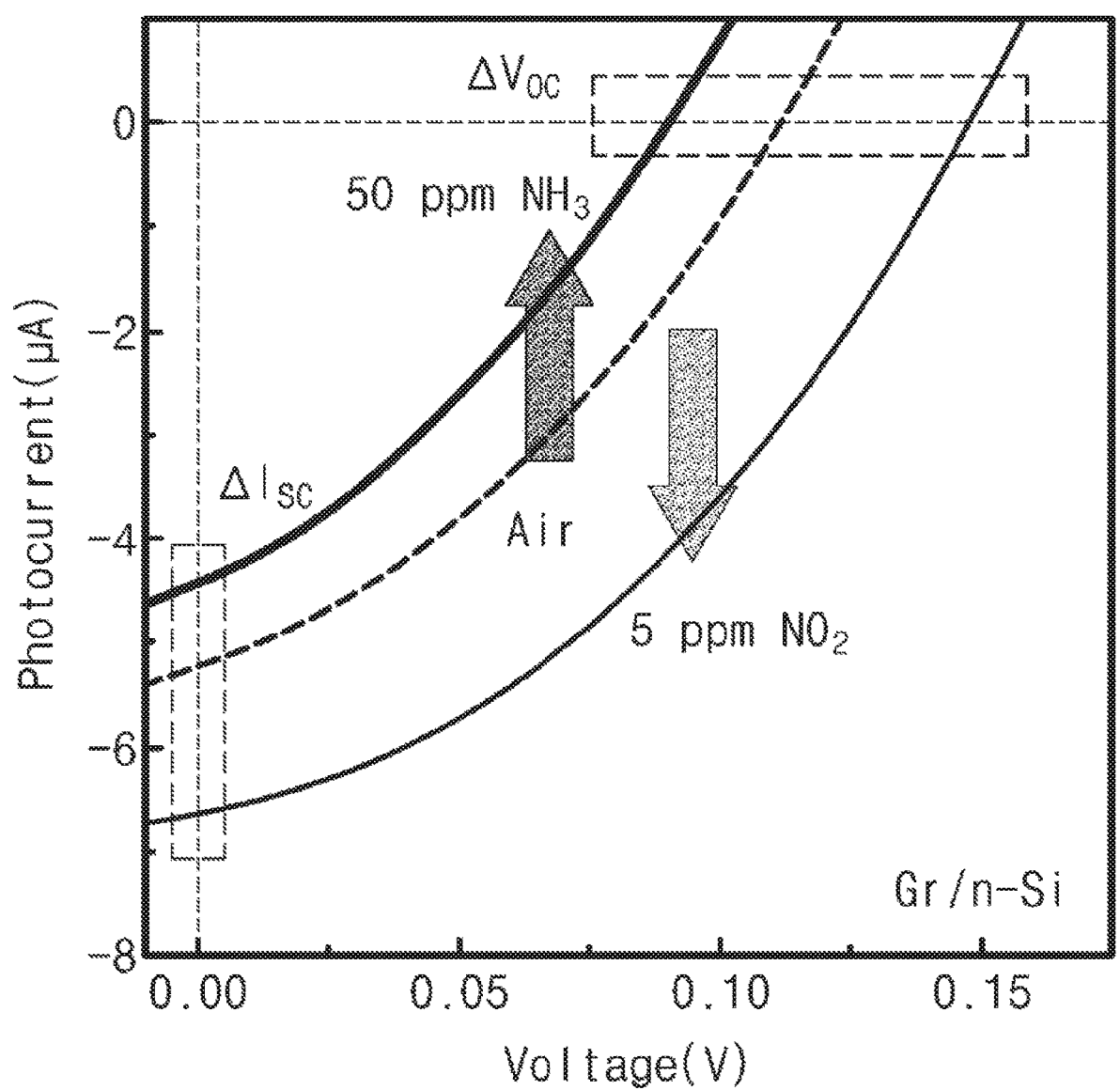
FIGS. 3A and 3B are graphs illustrating photocurrent changes for gas types of Examples 1 to 3.
Figure 3B:
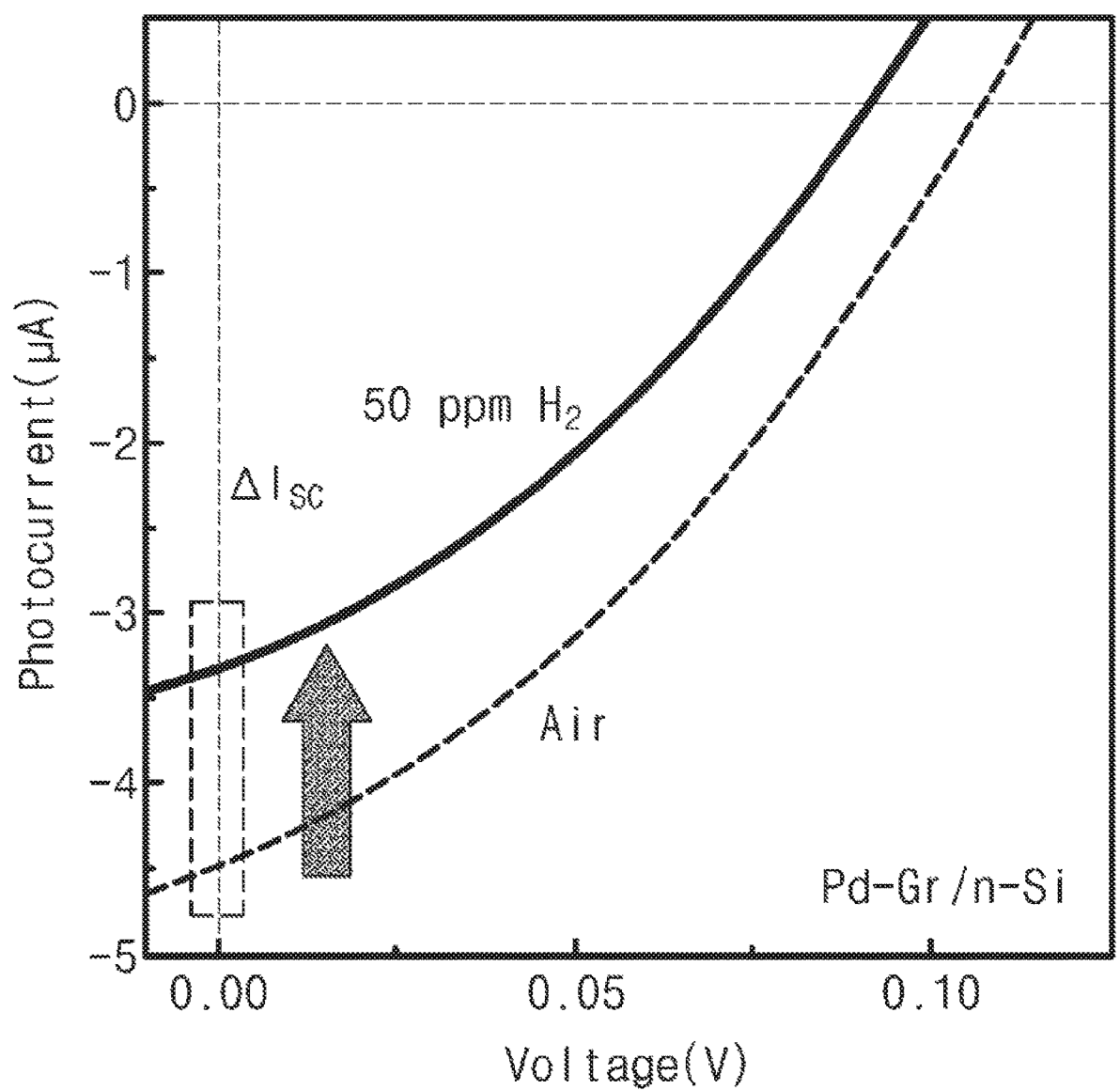
Figure 4A:
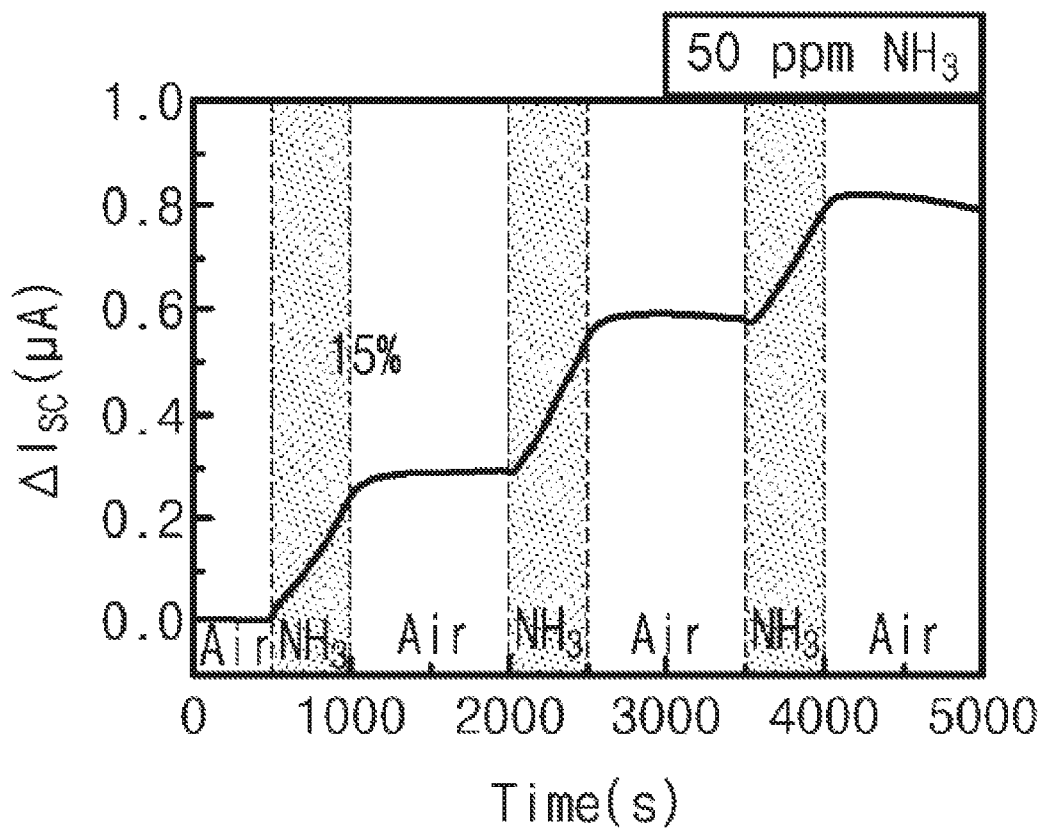
FIG. 4A to 4C are graphs illustrating photocurrent changes over time based on the gas types of Examples 1 to 3.
Figure 4A:
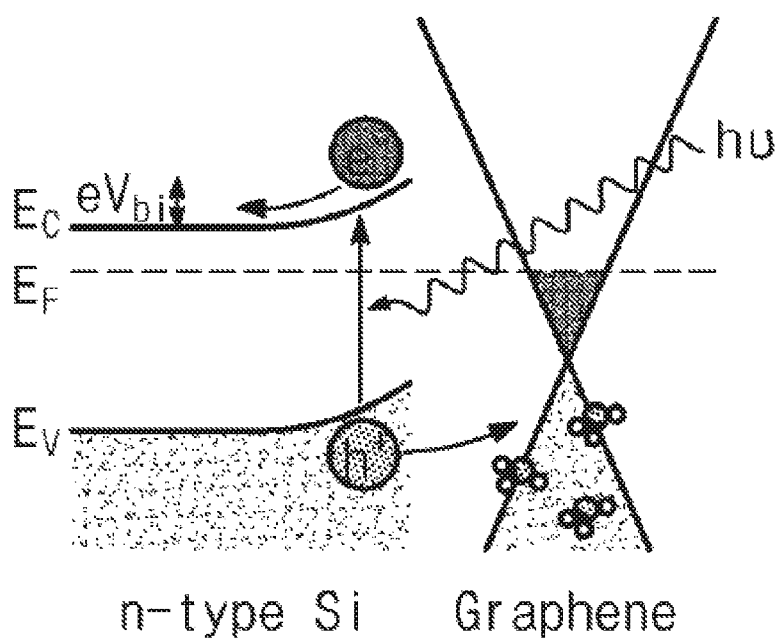
Figure 4B:
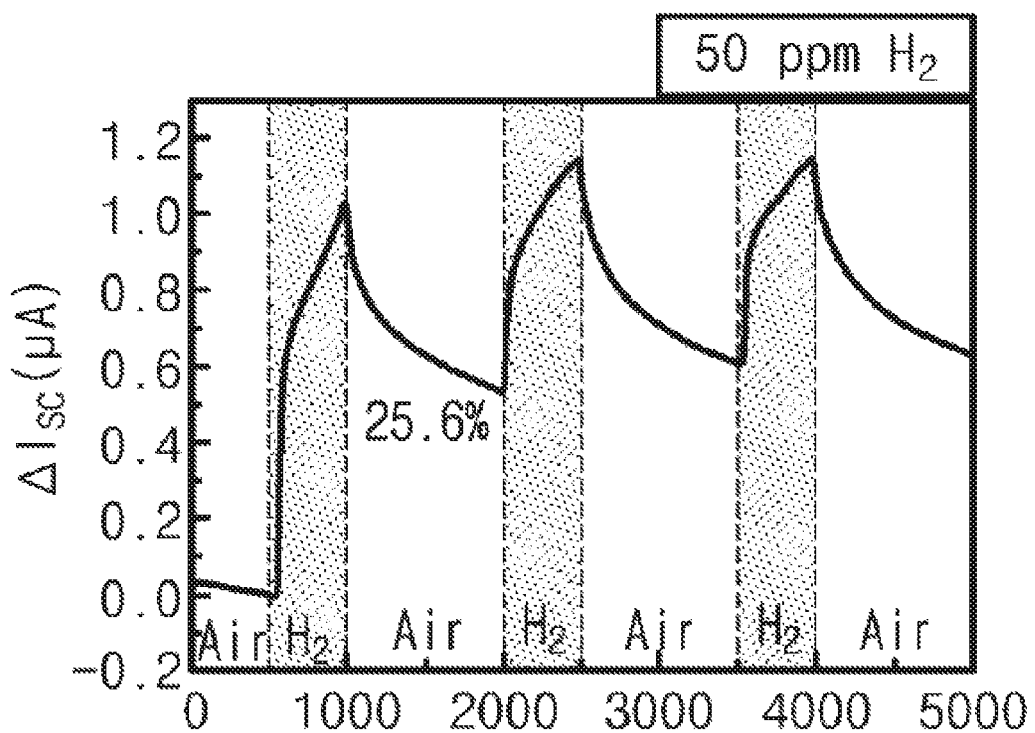
Figure 4B:
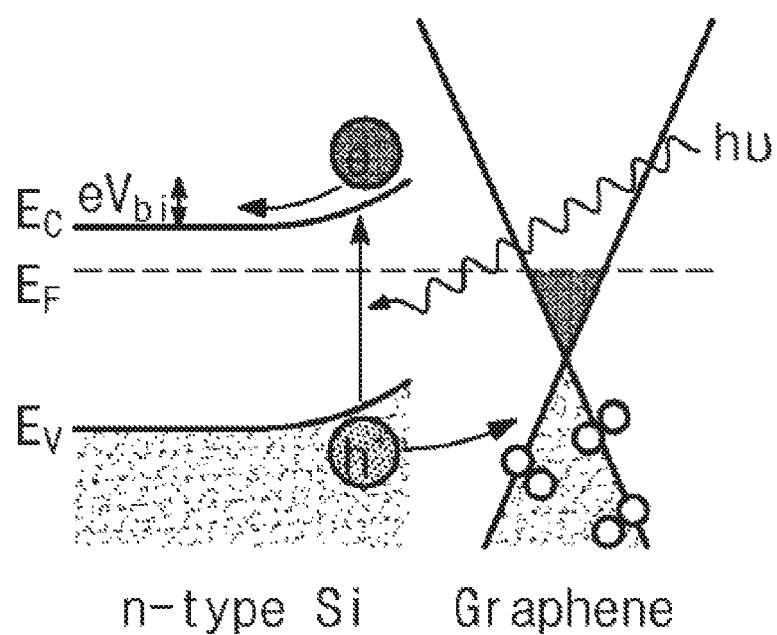
Figure 4C:
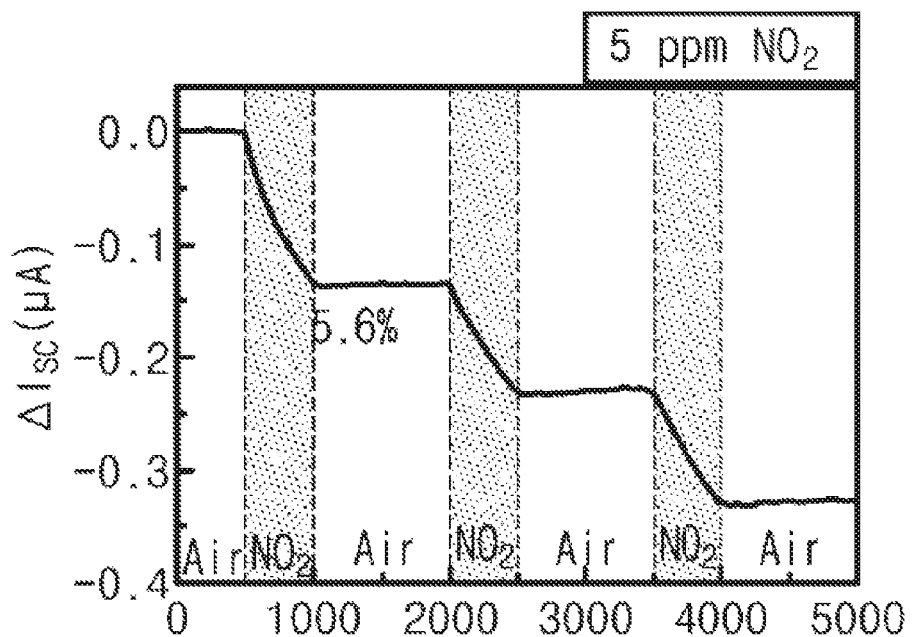
Figure 4C:
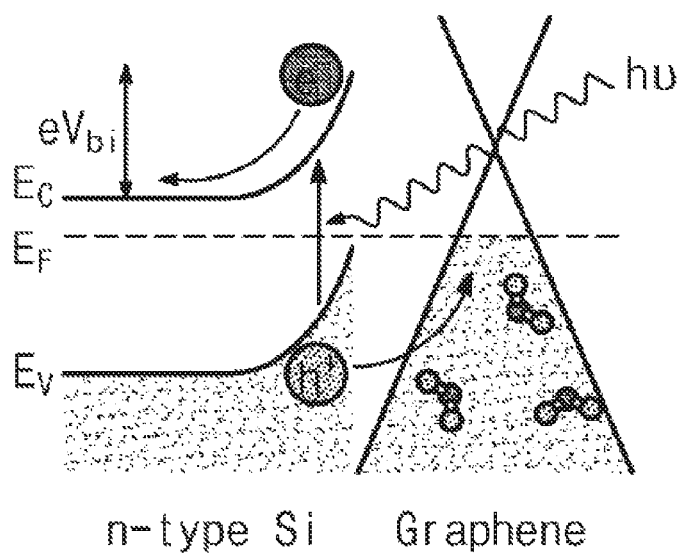

FIGS. 3A and 3B are graphs illustrating photocurrent changes for gas types of Examples 1 to 3, and FIG. 4A to 4C are graphs illustrating photocurrent changes over time based on the gas types of Examples 1 to 3.

FIGS. 3A and 3B are the graphs comparing a photocurrent change when dry air flows with photocurrent changes when NH3, NO2, and H2, which are used as a chemical substance, flow.

Referring FIG. 3A, when dry air flows under light irradiation, in current-voltage characteristics of a graphene/n-Si device, the photocurrent flows at 0V. In this case, when NH3 gas which is a type giving electrons to the graphene flows, a work function of the graphene decreases and a band gradient decreases based on the decrease of the graphene work function, and the amount of the photocurrent decreases.

On the contrary, when NO2 gas which is a type receiving electrons from the graphene flows, the work function of the graphene increases and the band gradient increases based on the increase of the graphene work function, and the amount of the photocurrent increases. This may confirm that the sensor operates with the proposed driving principle.

Referring to FIG. 3B, when H2 gas which is the type giving electrons to the graphene flows, the work function of the graphene decreases and the band gradient decreases based on the decrease of the graphene work function, and the amount of the photocurrent decreases.

FIG. 4A shows photocurrent changes when dry air and NH3 of 50 ppm flow over time.

Referring to FIG. 4A, an upper portion of the graphene is changed into a p-doped state by NH3 gas, the amount of a built-in potential of a Schottky junction decreases, and the amount of the photocurrent decreases. Thus, presence of the chemical substance may be confirmed.

FIG. 4B shows photocurrent changes when dry air and H2 of 50 ppm flow over time.

Referring to FIG. 4B, H2 gas is adsorbed to Pd of the upper portion of the graphene and Pd—Hx is formed. Then, the upper portion of the graphene is changed into the p-doped state, the amount of the built-in potential of the Shottky junction decreases, and the amount of the photocurrent decreases. Thus, presence of hydrogen may be confirmed.

FIG. 4C shows current changes when dry air and NO2 of 5 ppm flow over time.

Referring to FIG. 4C, the upper portion of the graphene is changed into an n-doped state by NO2 gas, the amount of a built-in potential increases, and the amount of the photocurrent increases. Thus, presence of the chemical substance may be confirmed.

Example 4

For confirming presence of H2, Example 4 was carried out the same as Example 3 (after junction of the graphene and the n-Si, Pd was deposited on the surface of the graphene to manufacture the detecting sensor). H2 flowed at a concentration of 1, 5, 50, 500, or 1,000 ppm and was sensed, respectively.

Figure 5:
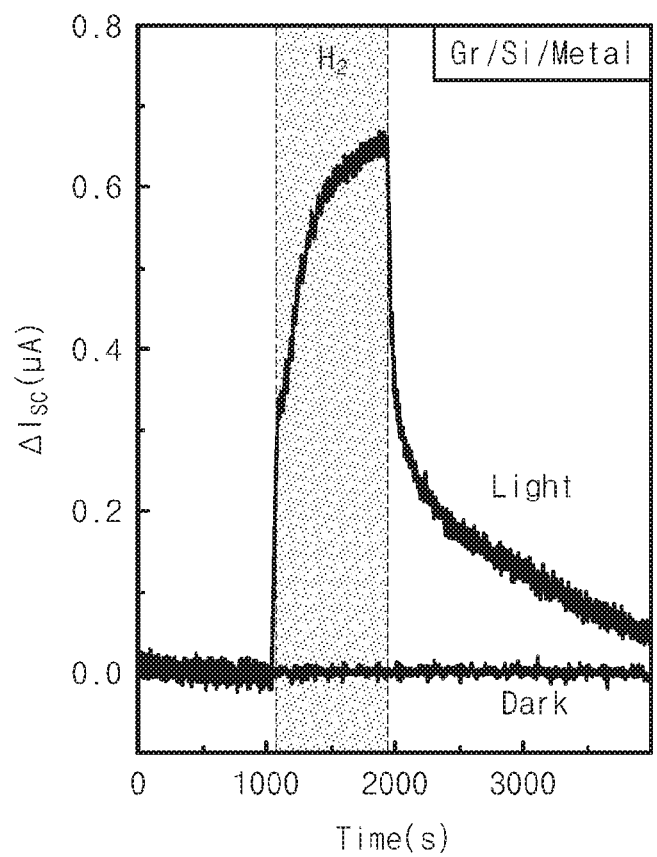
FIG. 5 is a sensing graph of hydrogen based on presence or absence of light using a detecting sensor of Example 4.

FIG. 5 is a sensing graph of hydrogen based on presence or absence of light using a detecting sensor of Example 4.

Figure 6:
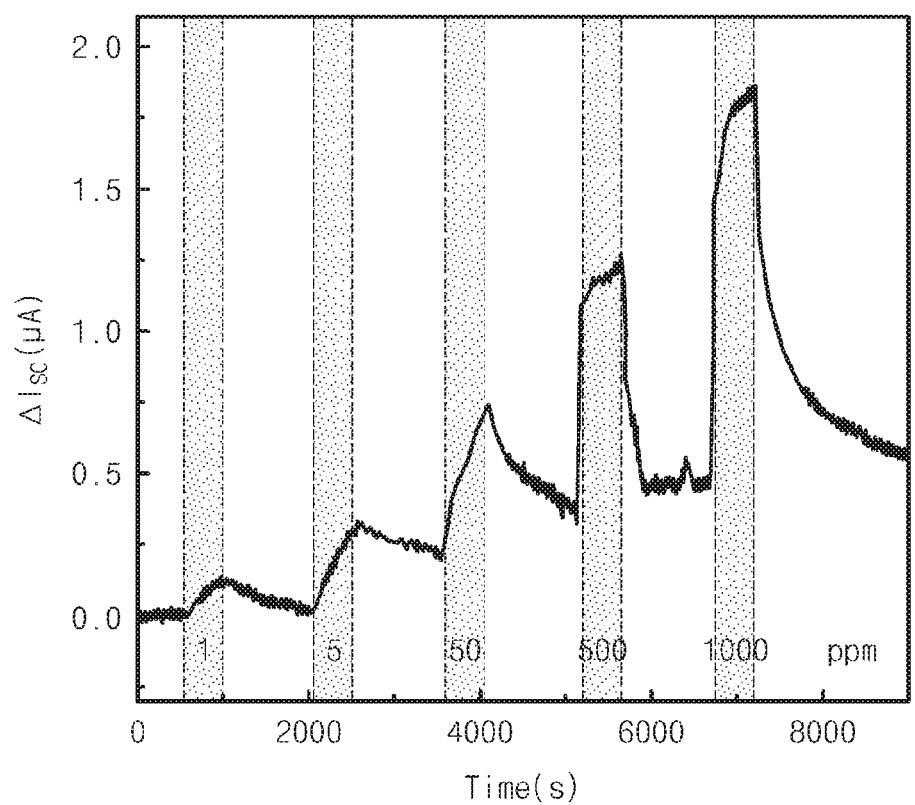
FIG. 6 is a graph illustrating photocurrent changes based on hydrogen concentrations using the detecting sensor of Example 4.

FIG. 6 is a graph illustrating photocurrent changes based on hydrogen concentrations using the detecting sensor of Example 4.

FIG. 5 shows photocurrent changes based on presence and absence of light while H2 of 1,000 ppm flows. When light is absent (a lower line), hydrogen is not sensed because a current does not flow at 0V.

On the other hand, when light is present (an upper line), hydrogen is sensed due to the photocurrent generated by light at 0V.

Referring to FIG. 6, the photocurrent changes are measured while increasing hydrogen (H2) concentrations over time under light irradiation. Hydrogen of 1, 5, 50, 500, or 1,000 ppm flows, respectively. When hydrogen of 1 ppm flows, the photocurrent flows, and therefore hydrogen is detected even at a small concentration.

According to an embodiment of the present disclosure, the detecting sensor detects the chemical substance by changing the photocurrent generated by the light without a driving voltage and is capable of operating without power.

In addition, according to an embodiment of the present disclosure, as the graphene having an atomic layer thickness instead of the conventional bulk semiconductor is used, the detecting sensor is capable of detecting the chemical substance, where the Fermi energy level is changed by the chemical substance adsorbed or desorbed on the surface of the graphene and the amount of the photocurrent in the detecting sensor is changed.

Also, in the present disclosure, important technological and industrial effects may be expected by suggesting a new device structure, a driving principle, and a measurement method. In detail, (1) power consumption may be minimized as the sensor operates through the change of the photocurrent without the driving voltage, (2) availability of technology is enhanced by suggesting various graphene-semiconductor structures having the heterojunction, and (3) the sensor may be miniaturized by an ultra-thin structure having atomic layer unit.

The foregoing detailed description is illustrative of the present disclosure. In addition, the foregoing is intended to illustrate and explain the preferred embodiments of the present disclosure, and the present disclosure may be used in various other combinations, modifications, and environments. That is, it is possible to make changes or modifications within the scope of the inventive concept disclosed in this specification, within the scope of the disclosure, and/or within the skill and knowledge of the art. The embodiments described herein are intended to illustrate the best mode for implementing the technical idea of the present disclosure and various modifications required for specific applications and uses of the present disclosure are also possible. Accordingly, the detailed description of the present disclosure is not intended to limit the present disclosure to the disclosed embodiments. It is also to be understood that the appended claims are intended to cover such other embodiments.

What is claimed is:

1. A method of determining an electronic property of a chemical substance without power, the method comprising:
    flowing an air comprising the chemical substance to a detecting sensor comprising a bottom electrode, a light absorbing layer comprising n-Si directly disposed on the bottom electrode, an insulating layer directly disposed on a first portion of the light absorbing layer, a top electrode directly disposed on the insulating layer, and a graphene layer directly disposed on a second portion of the light absorbing layer to form a heterojunction therebetween and the graphene layer extending such that it is connected to the top electrode, while irradiating a light to the detecting sensor;
    measuring a photocurrent generated by a photoreaction in the heterojunction between the graphene layer and the light absorbing layer comprising n-Si in response to the irradiating of the light absorbing layer in the air comprising the chemical substance without applying a driving voltage to the heterojunction;
    measuring a control photocurrent generated from the light absorbing layer in a control air not comprising the chemical substance while irradiating the light to the detecting sensor;
    and determining the electronic property of the chemical substance as electron-giving when the photocurrent decreases or as electron-receiving when the photocurrent increases compared to the control photocurrent measured when the control air not comprising the chemical substance flows to the detecting sensor, thereby detecting a presence of the chemical substance according to a change in the photocurrent,
    wherein the graphene layer is prepared by a chemical vapor deposition and is not a reduced graphene oxide layer and
    wherein the photocurrent generated with 5 ppm of $NO_2$ is at least 1 µA.

2. The method of claim 1, wherein a built-in potential is generated by a Fermi energy level difference at a Schottky junction interface between the graphene layer and the first portion of the light absorbing layer when the light having an energy of bandgap of the light absorbing layer or more is irradiated to the light absorbing layer.

3. The method of claim 2, wherein the Fermi energy level changes as the chemical substance is adsorbed or desorbed on a surface of the graphene layer.

4. The method of claim 1, wherein the chemical substance is $NH_3$ or $NO_2$.

5. The method of claim 1, wherein Pd or Pt is deposited on a surface of the graphene and the chemical substance is $H_2$.

* * * * *